(12) United States Patent
Angeletakis

(10) Patent No.: US 6,300,390 B1
(45) Date of Patent: *Oct. 9, 2001

(54) DENTAL RESTORATIVE COMPOSITE

(75) Inventor: Christos Angeletakis, Orange, CA (US)

(73) Assignee: Kerr Corporation, Orange, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 09/306,628

(22) Filed: May 6, 1999

Related U.S. Application Data

(63) Continuation-in-part of application No. 09/093,778, filed on Jun. 9, 1998, now Pat. No. 6,127,450, and a continuation-in-part of application No. 09/270,999, filed on Mar. 17, 1999, now Pat. No. 6,121,344.

(51) Int. Cl.$^7$ .................................................... A61K 6/083
(52) U.S. Cl. ........................... 523/116; 523/115; 524/140; 524/145; 524/219; 524/220; 524/307; 524/443; 524/520; 524/547; 524/559; 526/320; 526/326; 433/228.1
(58) Field of Search .................................... 523/115, 116; 524/140, 145, 219, 220, 307, 443, 520, 547, 559; 526/320, 326; 433/228.1

(56) References Cited

U.S. PATENT DOCUMENTS

| | | |
|---|---|---|
| Re. 35,264 | 6/1996 | Bennett . |
| 3,792,531 | 2/1974 | Rossi . |
| 3,859,421 | 1/1975 | Hucke . |
| 3,893,840 | 7/1975 | Wason . |
| 4,059,232 | 11/1977 | Engels . |
| 4,117,981 | 10/1978 | Engels . |
| 4,129,261 | 12/1978 | Engels et al. . |
| 4,132,806 | 1/1979 | Wason . |
| 4,156,766 | 5/1979 | Feldt . |
| 4,157,920 | 6/1979 | Wason et al. . |
| 4,161,455 | 7/1979 | Wason . |
| 4,164,794 | 8/1979 | Spector et al. . |
| 4,177,563 | 12/1979 | Schmitz-Josten et al. . |
| 4,197,234 | 4/1980 | Temin . |
| 4,202,813 | 5/1980 | Wason . |
| 4,215,033 | 7/1980 | Bowen . |
| 4,259,117 | * 3/1981 | Yamauchi et al. ............... 433/228.1 |
| 4,260,454 | 4/1981 | Wason et al. . |
| 4,292,029 | 9/1981 | Craig et al. . |
| 4,303,205 | 12/1981 | Geiger et al. . |
| 4,336,245 | 6/1982 | Wason . |
| 4,345,057 | 8/1982 | Yamabe et al. . |
| 4,362,681 | 12/1982 | Spector et al. . |
| 4,375,967 | 3/1983 | Schaefer . |
| 4,380,432 | 4/1983 | Orlowski et al. . |
| 4,396,476 | 8/1983 | Roemer et al. . |
| 4,407,984 | 10/1983 | Ratcliffe et al. . |
| 4,411,625 | 10/1983 | Koblitz et al. . |
| 4,422,880 | 12/1983 | Wason et al. . |
| 4,433,958 | 2/1984 | Fellman et al. . |
| 4,496,106 | 1/1985 | Gross . |
| 4,499,251 | 2/1985 | Omura et al. . |
| 4,503,169 | 3/1985 | Randklev . |
| 4,514,174 | 4/1985 | Dougherty et al. . |
| 4,515,930 | 5/1985 | Omura et al. . |
| 4,525,493 | 6/1985 | Omura et al. . |
| 4,537,940 | 8/1985 | Omura et al. . |
| 4,539,382 | 9/1985 | Omura et al. . |
| 4,544,683 | 10/1985 | Müller et al. . |
| 4,547,531 | 10/1985 | Waknine . |
| 4,551,486 | 11/1985 | Tateosian et al. . |
| 4,558,825 | 12/1985 | John et al. . |
| 4,609,687 | 9/1986 | Schwabe et al. . |
| 4,612,384 | 9/1986 | Omura et al. . |
| 4,650,847 | 3/1987 | Omura et al. . |
| 4,711,913 | 12/1987 | Tateosian et al. . |
| 4,722,947 | 2/1988 | Thanawalla et al. . |
| 4,745,138 | 5/1988 | Thanawalla et al. . |
| 4,756,862 | 7/1988 | Spector et al. . |
| 4,793,809 | 12/1988 | Sigler et al. . |
| 4,801,528 | 1/1989 | Bennett . |
| 4,813,875 | 3/1989 | Hare . |
| 4,839,401 | 6/1989 | Waknine . |
| 4,846,165 | 7/1989 | Hare et al. . |
| 4,857,111 | 8/1989 | Haubennestel et al. . |
| 4,863,977 | 9/1989 | Tateosian et al. . |
| 4,936,775 | 6/1990 | Bennett . |
| 4,957,554 | 9/1990 | Mathers et al. . |
| 4,978,640 | 12/1990 | Kelly . |
| 5,055,497 | 10/1991 | Okada et al. . |

(List continued on next page.)

OTHER PUBLICATIONS

Cabot Corporation, CAB–O–SIL TS–530 Treated Fumed Silica., Technical Data, Jul. 1989.

Dennis Miller, Cabot Corporation, CAB–O–SIL® Fumed Silica Properties and Functions, pp. 3–5.

Degussa Corporation, Technical Data for AEROSIL® Types.

S. Inokoshi, "Posterior Restorations: Ceramics or Composites?", Transactions Third International Congress on Dental Materials, Ed. H. Nakajima, Y. Tani JSDMD 1997.

*Primary Examiner*—Peter Szekely
(74) *Attorney, Agent, or Firm*—Wood, Herron & Evans, LLP

(57) ABSTRACT

The present invention provides a resin-based dental restorative that exhibits low volumetric shrinkage, high filler loading and the high strength required for load bearing restorations, yet maintains a glossy appearance, even after substantial wear. To this end, a dispersant is mixed with a methacrylate resin and a structural filler having a mean particle size between about 0.05 μm and about 0.50 μm. The composite is useful in stress bearing restorations and in cosmetic restorations. The structural filler used is typically ground to a mean particle size of less than 0.5 μm and also includes a microfill having a mean particle size less than 0.05 μm to improve handling and mechanical characteristics. The preferred dental composites maintain their surface finish even after substantial use and also have the strength properties of hybrid composite resins.

18 Claims, No Drawings

U.S. PATENT DOCUMENTS

| | | |
|---|---|---|
| 5,062,577 | 11/1991 | Schmitt et al. . |
| 5,065,946 | 11/1991 | Nishida et al. . |
| 5,125,971 | 6/1992 | Nonami et al. . |
| 5,130,463 | 7/1992 | Haubennestel et al. . |
| 5,133,508 | 7/1992 | Stehr et al. . |
| 5,134,175 | 7/1992 | Lucey . |
| 5,151,218 | 9/1992 | Haubennestel et al. . |
| 5,171,147 | 12/1992 | Burgess . |
| 5,177,120 | 1/1993 | Hare et al. . |
| 5,180,757 | 1/1993 | Lucey . |
| 5,210,109 | 5/1993 | Tateosian et al. . |
| 5,211,748 | 5/1993 | Robinson et al. . |
| 5,218,070 | 6/1993 | Blackwell . |
| 5,221,202 | 6/1993 | James . |
| 5,335,867 | 8/1994 | Stehr et al. . |
| 5,338,773 | 8/1994 | Lu et al. . |
| 5,367,002 * | 11/1994 | Huang et al. ......................... 523/116 |
| 5,399,782 | 3/1995 | Leppard et al. . |
| 5,501,827 | 3/1996 | Deeney et al. . |
| 5,502,087 | 3/1996 | Tateosian et al. . |
| 5,534,559 | 7/1996 | Leppard et al. . |
| 5,536,871 | 7/1996 | Santhanam . |
| 5,547,379 | 8/1996 | Hasel . |
| 5,554,030 | 9/1996 | Ario et al. . |
| 5,556,038 | 9/1996 | Nakamura et al. . |
| 5,583,178 | 12/1996 | Oxman et al. . |
| 5,595,487 | 1/1997 | Ario et al. . |
| 5,596,025 | 1/1997 | Oxman et al. . |
| 5,604,626 | 2/1997 | Teowee et al. . |
| 5,609,675 | 3/1997 | Noritake et al. . |
| 5,610,712 | 3/1997 | Schmitz et al. . |
| 5,612,414 | 3/1997 | Becker et al. . |
| 5,616,650 | 4/1997 | Becker et al. . |
| 5,637,641 | 6/1997 | Becker et al. . |
| 5,661,222 | 8/1997 | Hare . |
| 5,674,513 | 10/1997 | Snyder, Jr. et al. . |
| 5,697,390 | 12/1997 | Garrison et al. . |
| 5,708,051 | 1/1998 | Erdrich et al. . |
| 5,710,194 | 1/1998 | Hammesfahr et al. . |
| 5,733,997 | 3/1998 | Becker et al. . |
| 5,750,628 | 5/1998 | Becker et al. . |
| 5,760,102 | 6/1998 | Hall et al. . |
| 5,767,218 | 6/1998 | Becker et al. . |
| 5,807,954 | 9/1998 | Becker et al. . |
| 5,830,951 | 11/1998 | Fiedler . |
| 5,837,752 | 11/1998 | Shastri et al. . |
| 5,838,483 | 11/1998 | Teowee et al. . |
| 5,843,348 | 12/1998 | Giordano . |
| 5,849,270 | 12/1998 | Podszun et al. . |
| 5,861,445 | 1/1999 | Xu et al. . |
| 6,121,344 * | 9/2000 | Angeletakis et al. ................ 523/116 |
| 6,127,450 * | 10/2000 | Angeletakis ......................... 523/116 |

\* cited by examiner

DENTAL RESTORATIVE COMPOSITE

CROSS REFERENCE TO RELATED APPLICATION

This application is a continuation-in-part of U.S. Pat. Ser. No. 09/093,778, now U.S. Pat. No. 6,127,450 filed Jun. 9, 1998, and entitled "Dental Restorative Composite", which is incorporated by reference herein in its entirety, and a continuation-in-part of U.S. Pat. Ser. No. 09/270,999, now U.S. Pat. No. 6,121,344 filed Mar. 17, 1999, and entitled "Optimnum Paficle Sized Hybrid Composite", which is incorporated by reference herein in its entirety.

FIELD OF THE INVENTION

This invention relates to resin-based dental restoratives, and more specifically to restorative compositions incorporating uniformly dispersed submicron sized reinforcing particulate which exhibit high condensability and strength, low volumetric shrinkage, improved wear/abrasion resistance and improved gloss retention in clinical use.

BACKGROUND OF THE INVENTION

In dentistry, practitioners use a variety of restorative materials to create crowns, veneers, direct fillings, inlays, onlays and splints. Posterior and anterior tooth restoration is typically accomplished by excavating a tooth that has decayed or is otherwise in need of repair to form a cavity. This cavity is filled with a paste material, which is then compacted and shaped to conform to the original contour of the tooth. The paste is then hardened, typically by exposure to actinic light. The paste material is a tooth colored, packable, light curable, polymerizable restorative composition comprising a highly filled material.

Tooth colored dental restorative composites are usually composed of dispersions of glass filler particles below 50 $\mu$m in methacrylate-type monomer resin. Splintered pre-polymerized particles, which are ground suspensions of silica in pre-polymerized dental resins, may also be used. Additives such as pigments, initiators and stabilizers have also been used in these types of composites. Because the glass particle surface is generally hydrophilic, and because it is necessary to make it compatible with the resin for mixing, the glass filler is treated with a silane to render its surface hydrophobic. The silane-treated filler is then mixed with the resin at a proportion (load) to give a paste with a consistency considered usable, that is to allow the paste to be shaped without it flowing under its own weight during typical use. This paste is then placed on the tooth to be restored, shaped and cured to a hardened mass by chemical or photochemical initiation of polymerization. After curing, the mass has properties close to the structure of a tooth. The restorative composites may be dispersion reinforced, particulate reinforced, or hybrid composites.

Dispersion reinforced composites include a reinforcing filler of, for example, fumed silica having a mean particle size of about 0.05 $\mu$m or less, with a filler loading of about 30%–45% by volume. Because of the small particle size and high surface area of the filler, the filler loading into the resin is limited by the ability of the resin to wet the filler. Consequently, the filler loading is limited to about 45% by volume. Due to the low loading, the filler particles are not substantially in contact with one another. Thus, the primary reinforcing mechanism of such dispersion reinforced composites is by dislocation of flaws in the matrix around the filler. In dispersion reinforced materials, the strength of the resin matrix contributes significantly to the total strength of the composite. In dentistry, dispersion reinforced composite resins or microfills are typically used for cosmetic restorations due to their ability to retain surface luster. Typically, these microfill resins use free radical-polymerizable resins such as methacrylate monomers, which, after polymerization, are much weaker than the dispersed filler. Despite the dispersion reinforcement, microfill resins are structurally weak, limiting their use to low stress restorations.

One example of a dispersion reinforced composite is HELIOMOLAR®, which is a dental composite including fumed silica particles on the order of 0.05 $\mu$m mean particle size and rare earth fluoride particle on the order of less than 0.2 $\mu$m mean particle size. HELIOMOLAR® is a iadiopaque microfill-type composite. The rare earth fluoride particles contribute to both flexural strength and radiopacity.

Particulate reinforced composites typically include a reinforcing filler having an average particle size greater than about 0.6 $\mu$m and a filler loading of about 60% by volume. At these high filler loadings, the filler particles begin to contact one another and contribute substantially to the reinforcing mechanism due to the interaction of the particles with one another and to interruption of flaws by the particles themselves. These particulate reinforced composite resins are stronger than microfill resins. As with the dispersion reinforced composites, the resin matrix typically includes methacrylate monomers. However, the filler in particulate reinforced composites has a greater impact on the total strength of the composite. Therefore, particulate reinforced composites are typically used for stress bearing restorations.

Another class of dental composites, known as hybrid composites, include the features and advantages of dispersion reinforcement and those of particulate reinforcement. Hybrid composite resins contain fillers having an average particle size of 0.6 $\mu$m or greater with a microfiller having an average particle size of about 0.05 $\mu$m or less. HERCULTLTE®XRV (Kerr Corp.) is one such example. HERCULITE® is considered by many as an industry standard for hybrid composites. It has an average particle size of 0.84 $\mu$m and a filler loading of 57.5% by volume. The filler is produced by a wet milling process that produces fine particles that are substantially contaminant free. About 10% of this filler exceeds 1.50 $\mu$m in average particle size. In clinical use, the surface of HERCULITE® turns to a semi-glossy matte finish over time. Because of this, the restoration may become distinguishable from normal tooth structure when dry, which is not desirable for a cosmetic restoration.

Another class of composites, flowable composites, have a volume fraction of structural filler of about 10% to about 30% by volume. These flowable composites are mainly used in low viscosity applications to obtain good adaptation and to prevent the formation of gaps during the filling of a cavity.

In U.S. Pat. No. 6,121,344 filed Mar. 17, 1999 and entitled "Optimum Particle Sized Hybrid Composite", which is incorporated by reference herein in its entirety, it was found that resin-containing dental composites that incorporate a main structural filler of ground particles of average particle size at or below the wavelength of light (between about 0.05 $\mu$m to about 0.5 $\mu$m) have the high strength required for load bearing restorations, yet maintain a glossy appearance in clinical use required for cosmetic restorations. Composites containing a main structural filler with average particle size of about 1.0 $\mu$m or greater do not provide a glossy surface.

Various methods of forming submicron particles, such as precipitation or sol gel methods, are available to produce particulate reinforcing fillers for hybrid composites. However, these methods do not restrict the particle size to at or below the wavelength of light to produce a stable glossy surface. U.S. Pat. No. 5,600,67 to Noritake et al., shows an inorganic filler composition of 60%–99% by weight of spherical oxide particles having a diameter between 0.1–1.0 μm, and 1%–40% by weight of oxide particles having a mean particle diameter of less than 0.1 μm. This filler is manufactured by a chemical sol gel process. The particle size range includes particle sizes up to 1.0 μm and thug a dental composite using such filler will not provide a glossy surface in clinical use. The particles formed by the sol-gel process are spherical as shown in FIGS. 2A and 2B. The formulations described are designed to improve mechanical performance, wear and surface roughness of restorations, but do not provide for the retention of surface gloss in clinical use. Clinical studies of this material have actually shown high wear rates of 22.4 μm per year, which cannot establish a stable surface (S. Inokoshi, "Posterior Restorations: Ceramics or Composites?" in *Transactions Third International Congress on Dental Materials* Ed. H. Nakajima, Y. Tani JSDMD 1997).

Comminution by a milling method may also be used for forming the submicron particles. The predominant types of milling methods are dry milling and wet milling. In dry milling, air or an inert gas is used to keep particles in suspension. However, fine particles tend to agglomerate in response to van der Waals forces, which limits the capabilities of dry milling. Wet milling uses a liquid such as water or alcohol to control reagglomeration of fine particles. Therefore, wet milling is typically used for comminution of submicron-sized particles.

A wet mill typically includes spherical media that apply sufficient force to break particles that are suspended in a liquid medium. Milling devices are categorized by the method used to impart motion to the media. The motion imparted to wet ball mills includes tumbling, vibratory, planetary and agitation. While it is possible to form submicron particles with each of these types of mills, the agitation or agitator ball mill is typically most efficient.

The agitator ball mill, also known as an attrition or stirred mill, has several advantages including high energy efficiency, high solids handling, narrow size distribution of the product output, and the ability to produce homogeneous slurries. The major variables in using an agitator ball mill are agitator speed, suspension flow rate, residence time, slurry viscosity, solid size of the in-feed, milling media size and desired product size. As a general rule, agitator mills typically grind particles to a mean particle size approximately $\frac{1}{1000}$ of the size of the milling media in the most efficient operation. To obtain mean particle sizes on the order of 0.05 μm to 0.5 μm, milling media having a size of less than 0.45 mm can be used. Milling media having diameters of 0.2 mm and about 0.6 mm are also available from Tosoh Ceramics, Bound Brook, N.J. Thus, to optimize milling, it is desired to use a milling media approximately 1000 times the size of the desired particle. This minimizes the time required for milling.

Previously, the use of a milling process to achieve such fine particle sizes was difficult due to contamination of the slurry by the milling media. By using yttria stabilized zirconia (YTZ or Y-TZP, where TZP is tetragonal zirconia polycrystal), the contamination by spalling from the milling media and abrasion from the mill is minimized. Y-TZP has a fine grain, high strength and a high fracture toughness. YTZ is the hardest ceramic and because of this high hardness, the YTZ will not structurally degenerate during milling. High strength Y-TZP is formed by sintering at temperatures of about 1550° C. to form tetragonal grains having 1–2 μm tetragonal grains mixed with 4–8 μm cubic grains and high strength (1000 MPa), high fracture toughness (8.5 MPa m$^{1/2}$) and excellent wear resistance. The use of Y-TZP provides a suitable milling media for providing relatively pure structural fillers having mean particle sizes less than 0.5 μm.

In U.S. Pat. No. 6,010,085 filed Mar. 17, 1999 and entitled "Agitator Mill and Method of Use for Low Contamination Grinding", and U.S. Pat. No. 5,979,805 filed Dec. 4, 1998 and entitled "Vibratory Mill and Method of Use for Low Contamination Grinding", both incorporated herein by reference in their entirety, there is described an agitator mill and vibratory mill, respectively, and method of use designed to grind structural fill to a size at or below the wavelength of light with minimal contamination.

Aside from the need for achieving highly pure structural filler of particle size at or below the wavelength of light, an additional factor to be considered in developing dental composites is that the coefficient of thermal expansion of the glass fillers used in resin-based composites is much closer to tooth structure than that of the resins. So it is desirable to limit the amount of the resin in a dental composite and maximize the amount of filler material. The main factor limiting the volume fraction (load) of the inorganic filler in highly filled suspensions is particle-particle interactions. Dispersants, through their ability to reduce interactions between particles can improve the flow (reduce the viscosity) of the suspension, therefore allowing a higher load. Dispersants in non-aqueous systems are believed to reduce particle interactions by a steric stabilization mechanism. A layer of the dispersant is adsorbed on the surface of the particles keeping them apart from one another, reducing the viscosity. The dispersant structure must contain a chain that allows for steric stabilization in the resin and it also must be strongly adsorbed on the particle surface. In U.S. Pat. No. 6,127,450 filed Jun. 9, 1998, and entitled "Dental Restorative Composite", which is incorporated by reference herein in its entirety, the use of phosphate-type dispersants is described for increasing the loading in a hybrid composite in which the main structural filler has an average particle size of about 1.0 μm. There is a need, however, to provide a dispersant that will be effective with a non-aqueous, highly filled suspension containing a main structural filler having a particle size at or below the wavelength of light.

In summary, the dental profession is in need of a dental restorative that has high load capabilities and high strength for load bearing restorations, yet maintains a glossy appearance in clinical use required for cosmetic restorations.

SUMMARY OF THE INVENTION

The present invention provides a resin-containing dental composite including a phosphate-based dispersant and structural filler of ground particles having an average particle size of between about 0.05 μm and about 0.5 μm that has high loading capability and the high strength required for load bearing restorations, yet maintains a glossy appearance in clinical use required for cosmetic restorations. Further, because the structural filler particles are ground, the particles are nonspherical, providing increased adhesion of the resin to the structural filler, thereby further enhancing the overall strength of the composite. Through the use of the phosphate-based dispersant and structural filler particles that are ground and that have an average particle size less than the wavelength of light, that is less than about 0.50 μm, the dental composite of the present invention provides good physical properties and the luster and translucency required for cosmetic restorations. Specifically, since the structural filler size is less than the wavelength of visible light, the surface of a dental restoration will reflect more light in some directions than in others even after wear of the composite by brushing. The visible light waves do not substantially interact with the structural filler particles protruding out of the surface of the composite, and therefore, haze is reduced and the luster of the surface is maintained even after substantial brushing.

Known methods of milling, agitator and vibratory milling, have been adapted for use in the field of dental composites. As adapted, these methods are capable of further reducing the average particle size of the HERCULITE® filler to an average particle size of between about 0.05 μm and 0.5 μm. The particle size is at or below the wavelength of light, which minimize interaction with light, thus producing a stable glossy surface in clinical use. The particles are still large enough to reinforce the composite by the particulate reinforcement mechanism, so the restorations are also stress bearing. The number of larger particles, above 0.5 μm in diameter, are also minimized to help produce the stable glossy surface.

Additionally, because the structural filler particles are ground to an average particle size between about 0.05 μm and about 0.50 μm, the particles interact with one another to strengthen the composite, in the manner of typical hybrid composites, to allow a composite of the present invention to be useful in stress bearing restorations.

In a preferred embodiment, the structural filler is ground, typically by agitator or vibratory milling, to the preferred mean particle size. As opposed to the particles formed by the known sol-gel process, the grinding of the structural filler results in nonspherical particles which due to their irregular shape interact with the polymerized resin to a much greater extent to increase adhesion of the resin to the structural filler and thereby increase the overall strength of the composite.

Agitator or vibratory milling with selected media and optimized parameters produces the required size particles, free of contamination in a narrow particle size distribution. This reduces the small percentage of particles above 0.5 μm that can contribute to producing a non-glossy surface in clinical use.

In accordance with a further aspect of the invention, microfill particles having an average particle size less than about 0.05 μm are added, preferably between about 1% by weight and about 15 by weight of the composite. The microfill particles contribute to dispersion reinforcement, fill the interstices between the larger structural filler particles reducing occluded volume, and provide a large surface area to be wetted by the resin to increase strength. The microfill particles also contribute to the flow properties of the uncured resin.

Suitable phosphate-based dispersants for use in the present invention include phosphoric acid esters according to the formula:

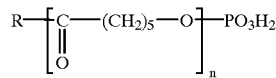

wherein R is a (meth)acrylate group functionalized radical, and wherein n represents the number of units of caprolactone.

DETAILED DESCRIPTION

The present invention, in a preferred form, is a dental restorative composite which includes a curable resin, a dispersant of the phosphoric acid ester type, and a ground structural filler having a mean particle size between about 0.05 μm and about 0.5 μm. The curable resin is preferably a photopolymerizable resin containing methacrylate monomers. Such methacrylate monomer resins are cured when exposed to blue visible light. The dental composite is applied to teeth by the dental practitioner and exposed to a visible light source to cure the resin. The cured resin has reduced shrinkage characteristics and a flexural strength higher than 90 MPa, and preferably greater than 100 MPa, which allows for the use of the resin in stress bearing applications.

To provide ground structural filler having a mean particle size of less than 0.5 μm, an extensive comminution step is required. Comminution may be performed in an agitator mill or vibratory mill, and more preferably an agitator mill or vibratory mill designed to minimize contamination, such as that described in U.S. Pat. No. 6,010,085 entitled "Agitator Mill and Method of Use for Low Contamination Grinding", C. Angeletakis, filed on Mar. 17, 1999 and incorporated herein by reference in its entirety, or that described in U.S. Pat. No. 5,979,805, entitled "Vibratory Mill and Method of Use for Low Contamination Grinding", C. Angeletakis, filed on Dec. 4, 1998 and incorporated herein by reference in its entirety. Comminution deagglomerates the structural filler particles by separating particles from clusters, decreases the size of the structural filler particles, eliminates large particles by breakage and increases the specific surface area of the structural filler particles by producing a large quantity of very fine particles. Size reduction with an agitator or vibratory mill occurs due to a combination of impact with the milling media, abrasion with the milling media and attrition of the particles.

Structural fillers suitable for use in the present invention include barium magnesium aluminosilicate glass, barium aluminoborosilicate glass, amorphous silica, silica-zirconia, silica-titania, barium oxide, quartz, alumina and other inorganic oxide particles.

Inclusion of a novel dispersant in dental composite formulations of the present invention results in increased filler loading and decreased viscosity, which after curing provides a dental restorative with reduced shrinkage, a lower coefficient of thermal expansion and generally improved physical properties. Suitable dispersants useful in the present invention are phosphoric acid esters (including mono-, di- and tri-esters). Particularly, phosphoric acid esters useful in the present invention contains polymerizable groups and are selected from the following: a) a phosphoric acid ester containing a carboxylic acid ester group and an ether group, and b) a phosphoric acid ester containing a carboxylic acid ester group and not containing an ether group. These dispersants are effective with nonaqueous, highly-filled suspensions containing polymerizable groups (e.g., acrylic and methacrylate esters) used for dental purposes and, more particularly, with highly-filled glass suspensions containing methacrylate resins. The dispersants useful in the present invention preferably comprise 5 weight percent or less of the composite paste. To obtain good uniformity of distribution of the dispersant in the final composite paste, the dispersant is first mixed with the resin, followed by the slow addition of the filler material.

The dispersant of the present invention is a phosphoric acid ester with the following general structure:

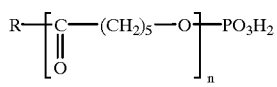

where R is a (meth)acrylate group functionalized radical, and wherein n represents the number of units of caprolactone.

The presence of the carboxylic acid ester group of the dispersant results in excellent compatibility with (meth)acrylate-baged resin systems. In a preferred embodiment, the dispersant of the present invention has the structure shown above, wherein R is one of the following:

Compound 1:R=oxyethyl methacryloyl-

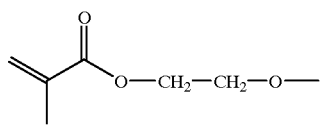

Compound 2:R=oxyethyl acryloyl-

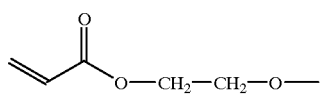

Compound 3:R=polyoxypropyl methacryloyl-

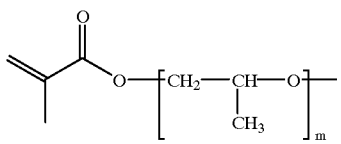

Compound 4:R=glyceryl dimethacryloyl-

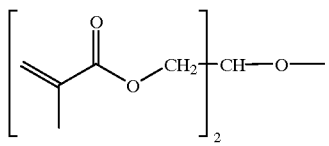

Compound 5:R=dipentaerythritol pentaacryloyl-

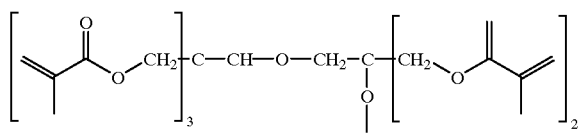

Compound 6:R=polyoxyethyl methacryloyl-

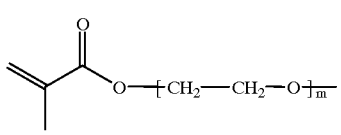

Each of Compounds 1–6 may be prepared in two steps. In the first step, the hydroxy functional methacrylate is condensed with caprolactone under ring-opening polymerization conditions in the presence of catalytic amounts of $SnCl_2$ (40–400 ppm) to prepare a polyester. In the second step, the polyester is reacted with polyphosphoric acid (117.5% concentration) at 65° C. to give the phosphoric acid ester. By way of example, the reaction sequence is shown below for the preparation of the hydroxyethyl methacrylate (HEMA) derivative Compound 1:

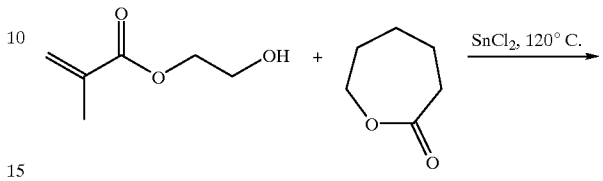

HEMA, MW=130.14 Caprolactone, MW=114.14

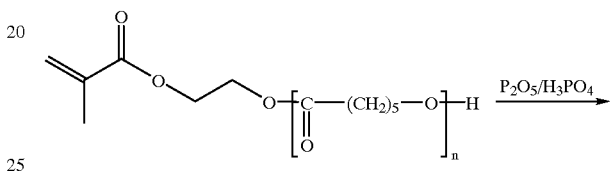

Polycaprolactone modified HEMA

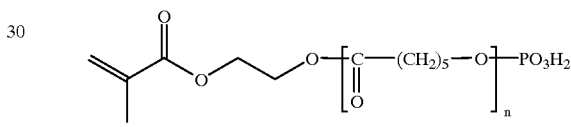

Compound 1: Polycaprolactone modified HEMA Phosphate

In a further preferred embodiment of the present invention, the dispersant is preferably added at about 0.5 to about 3.5 weight percent of the composite paste. The following examples will further illustrate this aspect of the present invention.

EXAMPLE

In a 4-neck reaction kettle containing an air flow tube, a thermocouple, a condenser and a stirrer, 26.0 parts by weight of hydroxyethyl methacrylate (HEMA) were combined with 114.1 parts by weight of caprolactone, 0.14 parts by weight of methyl ether of hydroquinone (MEHQ) and 0.007 parts by weight of stannous chlorde under a flow of dry air. The mixture was thermostated at 120° C. and stirring was continued for 18 hours. The disappearance of the caprolactone was monitored with HPLC (High Pressure Liquid Chromatography) using a reverse phase column with 70/30 acetonitrile/water as eluant. The resultant liquid polycaprolactone-modified HEMA was essentially colorless.

In a three neck flask equipped with a stirrer and a condenser under a constant flow of dry air, 70.0 grams of the above product (polycaprolactone-modified HEMA) was combined with 8.45 grams of 117.5% phosphoric acid. The mixture was heated with stirring for 4 hours at 70° C. A light yellow oil resulted. Titration with 0.1N NaOH showed that the phosphoric acid ester was formed.

Various methacrylate derivative prepared using the above procedures are listed in Table 1.

TABLE 1

Polycaprolactone-Modified Methacrylate Monophosphates

| Compound | Starting Material | Caprolactone: starting material (mole ratio) | Molecular Weight Average |
|---|---|---|---|
| 1a | Hydroxyethyl Methacrylate (HEMA) | 1:1 | 324 |
| 1b | HEMA | 2:1 | 438 |
| 1c | HEMA | 5:1 | 780 |
| 1d | HEMA | 7:1 | |
| 2 | Hydroxyethyl acrylate (HEA) | 5:1 | 766 |
| 3 | Polypropylene glycomethacrylate (PPGMA) | 5:1 | 713 |
| 4a | Glycerol Dimethacrylate (GDMA) | 2:1 | 536 |
| 4b | GDMA | 5:1 | 879 |
| 5a | Dipentaerythritol pentaacrylate DPEPA) | 2:1 | 713 |
| 5b | DPEPA | 5:1 | 1175 |
| 6a | Polyethylene glycol monomethacrylate (PEGM) | 0 | 459 |
| 6b | PEGM | 2:1 | 687 |
| 6c | PEGM | 5:1 | 1029 |

All of the above compounds may be used as dispersants in highly filled glass suspensions containing methacrylate resins. One control sample, two test samples and two comparative samples were prepared according the following method. A methacrylate resin, as described in Table 2, was introduced into a planetary mixer and thermostated to 50° C. It should be appreciated that alternative monomers to those listed in Table 2 may be utilized in the resin composition. For example, diethylene glycol dimethacrylate, tetraethylene glycol dimethacrylate, 1,6-hexanediol dimethacrylate, 1,12-odecanediol dimethacrylate, diurethane dimethacrylate (Rohamere 6661-0, Huls America, Somerset, N.J.), trimethylolpropane trimethacrylate, glyceryl dimethacrylate, eopentylglycol dimethacrylate. The phosphate ester dispersant with the general structure described above was then added to the resin, with the exception of the control sample, so as to comprise 1.5 wt. % of the total resin/filler mixture. The test samples were prepared with a 74.5 wt. % filler loading; the control sample was prepared with a 72 wt. % filler loading; and the comparative samples were prepared with an 80 wt. % filler loading. The planetary mixer was started for a few minutes to mix the resin phase and then the filler containing the physically admixed components listed in Table 3 was slowly added over a period of about 3 hours. Mixing was continued for another hour and the resultant paste was deaerated under attenuated oxygen pressure. Table 3 details the physical properties of the test sample pastes prepared along with the properties of control sample 1 and comparative samples 1 and 2. All measurements were carried out using standard ISO methods except where indicated, and the standard deviations are provided in parentheses.

TABLE 2

| Resin Composition | |
|---|---|
| BisGMA (Bisphenol A Diglycidyl ether dimethacrylate) | 3.0 wt. % |
| Triethylene Glycol Dimethacrylate | 24.7 wt. % |
| Ethoxylated Bisphenol A Dimethacrylate | 71.1 wt. % |
| 2-Ethylhexyl-4-(dimethylamino)benzoate | 0.49 wt. % |
| Camphorquinone | 0.17 wt. % |
| 2-Hydroxy-4-methoxy Benzophenone | 0.49 wt. % |
| (BHT) Butylated Hydroxytoluene | 0.05 wt. % |
| Total | 100 |

TABLE 3

Physical Properties of Pastes Prepared with Various Dispersants in a Planetary Mixer

| Dispersant, 1.5 Wt. % | Control Sample 1 None | Test Sample 1 1c | Test Sample 2 4b | Comparative Sample 1 1c | Comparative Sample 2 4b |
|---|---|---|---|---|---|
| Filler Mean Average Particle Size >50% ($\mu$m) | 0.41 | 0.41 | 0.43 | 1.0 | 1.0 |
| Filler Mean Average Particle Size >90% ($\mu$m) | 0.65 | 0.65 | 0.75 | 1.8 | 1.8 |
| Wt. % 20 nm Hydrophobic fumed silica | 4.0[1] | 5.0[2] | 5.0[2] | 4.0[1] | 4.0[1] |
| Wt. % 40 nm Fumed Silica, silanated[3] | 3.0 | 4.0 | 4.0 | 4.0 | 4.0 |
| Barium Aluminum Silicate, silanated | 65[4] | 65.5[4] | 65.5[4] | 72[5] | 72[5] |
| Wt. % Filler Load | 72 | 74.5 | 74.5 | 80 | 80 |
| Depth of Cure at 600 mW/cm$^2$, 4 mm diameter | 4.0 | 3.3 | 3.2 | 4.6 (0.1) | 4.1 (0.3) |
| Rockwell Hardness (15 T)[6] | 79.1 | 81.0 | — | 83.4 (0.1) | 83.9 (0.1) |
| Compressive Strength (MPa) | 381 (39) | 331 (32) | 334 (30) | 399 (21) | 408 (34) |
| Flexural Strength (MPa) | 120 (18.6) | 100 (16) | 139 (12) | 129 (12) | 125 (26) |
| Flexural Modulus (Mpa) | 9,521 (331) | 9,564 (654) | 11,043 (807) | 11,189 (968) | 10,571 (2,051) |
| Penetrometer (mm)[7] 0 g, (Needle, 1 mm) | 7.5 | 7.2 | 5.6 | >8.0 | 6 (0.2) |

TABLE 3-continued

Physical Properties of Pastes Prepared with Various Dispersants in a Planetary Mixer

| Dispersant, 1.5 Wt. % | Control Sample 1 None | Test Sample 1 1c | Test Sample 2 4b | Comparative Sample 1 1c | Comparative Sample 2 4b |
|---|---|---|---|---|---|
| Penetrometer (mm)[8] 0 g, (Flathead, 1 mm) | 4.3 | 3.5 | 2.0 | >8.0 | 4.3 (0.1) |
| Slump (cm) 400 g, 30 s | 2.6 | 2.6 | 2.4 | — | — |

[1]TS 530, available from Degussa Corp., Ridgefield Park, N.J.
[2]US 202, available from Degussa Corp., Ridgefield Park, N.J.
[3]OX-50, available from Degussa Corp., Ridgefield Park, N.J.
[4]GM27884 Raw glass (25% barium content) available from Schott Glasswerke, Landshut, Germany.
[5]SP345 Raw glass (30% barium content) available from Specialty Glass, Inc., Oldsmar, FL.
[6]Average of 3 measurements on the surface of a cylindrical sample 10 mm in diameter and 4 mm in height. The samples were light cured for 40 seconds, and stored in water for 24 hours at 37° C. prior to measurement.
[7]Precision Penetrometer (GCA Corp., Chicago, IL) with a 1 mm needle was used with no additional weight (0 g). The paste was placed in a mold 10 mm in diameter and 8 mm in height. Penetration was performed for 10 seconds. An average of 3 measurements is reported.
[8]Same test as above, but using a flat head rather than a needle, to simulate the effect of the impact from dental instruments having a flat head on the composite.

Surprisingly, it has been found that the behavior of dispersants differs markedly with the size of the main structural filler. In the comparative samples, the physical properties of the composites are essentially equivalent, with the main difference being the viscosity, as indicated by the penetrometer test. As Table 3 shows, however, dispersant 4b is significantly more effective in producing a paste with superior physical properties at high loads with a 0.4 μm sized filler than the 1c dispersant. Comparison of the penetrometer results show that although the 1c dispersant is more effective in reducing the viscosity of both size fillers, the difference is small in the case of the 0.4 μm fillers. The paste containing the 4b dispersant with the 0.4 μm filler, however, exhibits a substantially higher flexural strength and modulus. This difference is expected to result in better performance when the material is placed in vivo.

To further demonstrate the effects of various dispersants on the viscosity of a paste comprising a 0.4 μm filler system and on the final properties of the cured composite, seven dispersants prepared as described above were added in an amount of 1.5 wt. % to a paste prepared as described above comprising the components listed in Table 4, except mixing was performed for 60 seconds with a centrifugal type mixer, such as a Speed Mix type AM501T, available from Hauschild Engineering, Hamm, Germany. The mixing is achieved by applying two centrifugal forces, one in the center of the container, and one in the opposite direction a distance away from the container.

TABLE 4

0.4 μm Filler/Resin Paste Composition at 75% Filler Loading

| | |
|---|---|
| 0.4 μm Barium Aluminum Silicate Glass,[1] silanated | 66 wt. % |
| OX-50 Fumed Silica, silanated (40 nm)[2] | 4.0 wt. % |
| US202 Hydrophobic Fumed Silica (20 nm)[2] | 5.0 wt. % |
| Resin (Table 2) | 23.5 wt. % |
| Dispersant | 1.5 wt. % |
| Total | 100 |

[1]Mixture of 60 wt. % SP345 (Specialty Glass, Inc.) and 40 wt. % GM27884 (Schott Glasswerke).
[2]Mean average particle size.

Two comparative samples of a dispersant in a 1.0 μm filler system were also prepared in the same manner as the test samples, comprising the components listed in Table 5.

TABLE 5

1.0 μm Filler/Resin Paste Composition at 80% Filler Loading

| | |
|---|---|
| 1.0 μm Barium Aluminum Silicate Glass (SP345), silanated | 72.4 wt. % |
| OX-50 Fumed Silica, silanated (40 nm)[1] | 3.6 wt. % |
| US202 Hydrophobic Fumed Silica (20 nm)[1] | 4.0 wt. % |
| Resin (Table 2) | 18.5 wt. % |
| Dispersant | 1.5 wt. % |
| Total | 100 |

[1]Mean average particle size.

The properties of the pastes and cured composites for comparative samples 3–4 and test samples 3–9 are provided in Table 6.

TABLE 6

Physical Properties of Pastes Prepared with Various Dispersants in a Centrifugal Mixer

| | Comparative Sample 3 | Comparative Sample 4 | Test Sample 3 | Test Sample 4 | Test Sample 5 | Test Sample 6 | Test Sample 7 | Test Sample 8 | Test Sample 9 |
|---|---|---|---|---|---|---|---|---|---|
| Dispersant, 1.5 Wt. % | 1c | 4b | 1c | 2 | 4b | 5b | 6a | 6b | 6c |
| Wt. % Filler Load | 80 | 80 | 75 | 75 | 75 | 75 | 75 | 75 | 75 |
| Vickers Hardness | 571 | 591 | 478 | 512 | 484 | 544 | — | — | 480 |
| (N/mm$^2$)[1] | (9) | (3) | (5) | (7) | (20) | (20) | | | (28) |
| Flexural Strength | 121 | 135 | 127 | 130 | 139 | 93 | 110 | — | 119 |
| (MPa) | (27) | (18) | (7) | (23) | (12) | (15) | (21) | | (15) |
| Flexural Modulus | 12,897 | 13,597 | 10,837 | 10,070 | 10,720 | 10,730 | 11,134 | — | 10,034 |
| (MPa) | (408) | (549) | (640) | (560) | (389) | (670) | (560) | | (850) |
| Penetrometer (mm)[2] 0 g, (Needle, 1 mm) | — | 4.2 (0.1) | — | 7.2 | >8.0 | — | 2.7 (0.1) | 3.3 (0.4) | 7.5 (0.3) |
| Penetrometer (mm)[3] 0 g, (Flathead, 1 mm) | >8 | 1.0 (0) | >8 | 3.5 | 4.7 (0.6) | 3.6 (0.6) | 1.0 (0.5) | 0.7 (0.1) | 2.4 (0.2) |

[1]Average of 3 measurements on the surface of a cylindrical sample 10 mm in diameter and 2 mm in height. The samples were light cured for 60 seconds, and stored in water for 24 hours at 37° C. prior to measurement.
[2]Precision Penetrometer (GCA Corp., Chicago, IL) with a 1 mm needle was used with no additional weight (0 g). The paste was placed in a mold 10 mm in diameter and 8 mm in height. Penetration was performed for 10 seconds. An average of 3 measurements is reported.
[3]Same test as above, but using a flat head rather than a needle, to simulate the effect of the impact from dental instruments having a flat head on the composite.

Table 6 demonstrates that dispersant 4b provides an overall best physical profile when compared to the other dispersants listed when incorporated into a 0.4 μm filler system. The penetrometer data for the Compound 6 derivatives (Samples 7–9) suggest that increasing chain length of the caprolactone units improves the dispersant effect. When compared to the use of the dispersants in a 1.0 μm system, the 1c and 4b dispersants provided similar results in both filler systems. It should be noted, however, that a centrifugal type mixer was used to prepare the samples present in Table 6. The centrifugal mixer, by design, applies less shear to the components of the mixture than does a planetary mixer. As a result, the centrifugal type mixer does not fully mix the components, nor does it effectively break large agglomerates of filler particles. This is believed to decrease the effectiveness of the dispersants, and the filler components are not as effectively dispersed as they are in the planetary mixer. Insufficient dispersion of the filler by the mixer is expected to lead to decreased effectiveness of the dispersant. Thus, the results of Table 6 are believed to be less indicative of the effectiveness of the dispersants in a 0.4 μm filler system as compared to the results presented in Table 3.

While the present invention has been illustrated by the description of an embodiment thereof, and while the embodiment has been described in considerable detail, it is not intended to restrict or in any way limit the scope of the appended claims to such detail. Additional advantages and modifications will readily appear to those skilled in the art. For example, the quantity of the dispersant to be added to the resin/filler mixture will vary based on the particular compositions used for the resin and the filler. The invention in its broader aspects is therefore not limited to the specific details, representative method and illustrative examples shown and described. Accordingly, departures may be made from such details without departing from the scope or spirit of applicant's general inventive concept.

What is claimed is:

1. A dental restorative composition comprised of:
   between about 10% by volume and about 70% by volume of a ground structural filler having a men particle size between about 0.05 μm and about 0.50 μm, wherein the ground structural filler contains less than 50% by volume of particles above 0.5 μm in diameter, mean particle size;
   a polymerizable acrylic monomer; and
   a phosphoric acid ester dispersant.

2. The dental restorative composition of claim 1, wherein the phosphoric acid ester dispersant includes a polymerizable group and a carboxylic acid ester group.

3. The dental restorative composition of claim 1, wherein the phosphoric acid ester dispersant is a polycaprolactone-modified methacrylate monophosphate.

4. The dental restorative composition of claim 1, wherein the phosphoric acid ester dispersant comprises about 5 weight percent or less of the dental restorative composition.

5. A dental restorative comprised of:
   between about 10% by volume and about 70% by volume of a ground structural filler having a mean particle size between about 0.05 μm and about 0.50 μm, wherein the ground structural filler contains less than 50% by volume of particles above 0.5 μm in diameter, mean particle size;
   a polymerizable acrylic monomer; and
   a dispersant, wherein the dispersant is a phosphoric acid ester according to the formula:

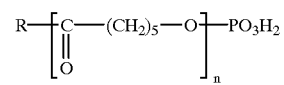

wherein R is a (meth)acrylate group functionalized radical and n represents the number of caprolactone units.

6. The dental restorative composition of claim 5, wherein R is a radical selected from the group consisting of: oxyethyl methacryloyl-, oxyethyl acryloyl-, polyoxypropyl methacryloyl-, glyceryl dimethacryloyl-, dipentaerythritol pentaacryloyl-, and polyoxyethyl methacryloyl-.

7. The dental restorative composition of claim 5, wherein the disperant comprises about 5 weight percent or less of the dental restorative composition.

8. The dental restorative of claim 5, wherein the dispersant is present in the range of about 0.5 to about 3.5 weight percent of the dental restorative.

9. The dental restorative of claim 5, wherein the dispersant is a polycaprolactone-modified methacrylate monophosphate present in the range of about 0.5 to about 3.5 weight percent of the dental restorative.

10. The dental composite of claim 5, wherein the cured resin composite has a flexural strength of at least 90 MPa.

11. The dental composite of claim 5, wherein the cured resin composite has a flexural strength of at least 100 MPa.

12. The dental composite of claim 5, wherein the cured resin composite has a gloss at a 60° measurement angle of about 30 or greater.

13. The dental composite of claim 5, wherein the ground structural filler contains less than 10% by volume of particles above 0.8 μm in diameter, mean particle size.

14. The dental composite of claim 5, further comprising between about 1.0 and about 10.0% by volume microfiller having a mean particle size of about 0.04 μm or less.

15. The dental composite of claim 14, wherein the microfiller includes between about 0.5% by volume and about 5.0% by volume particles having a mean particle size of approximately 0.04 μm and between about 0.5% by volume and about 5.0% by volume particles having a mean particle size of approximately 0.02 μm.

16. A method of restoring a tooth comprising the steps of:

preparing the tooth for restoration; and applying to the prepared tooth the dental restorative composite of claim 1.

17. A method of restoring a tooth comprising the steps of:

preparing the tooth for restoration; and applying to the prepared tooth the dental restorative composite of claim 5.

18. The dental composite of claim 5, wherein n=1–7.

* * * * *

UNITED STATES PATENT AND TRADEMARK OFFICE
CERTIFICATE OF CORRECTION

PATENT NO.    : 6,300,390 B1
DATED         : October 9, 2001
INVENTOR(S)   : Christos Angeletakis It is certified that error appears in the above-identified patent and that said Letters Patent is hereby corrected as shown below:

Column 1,
Line 11, reads "entitled "Optimnum Paficle Sized" and should read -- entitled "Optimum Particle Sized --

Column 2,
Line 15, reads "iadiopaque" and should read -- radiopaque --
Line 39, reads "HERCULTLTE®" and should read -- HERCULITE® --

Column 3,
Line 4, reads "No. 5,600,67" and should read -- No. 5,600,675 --
Line 10, reads "thug" and should read -- thus --

Column 5,
Line 15, reads "HERCULLITE®" and should read -- HERCULITE® --
Line 18, reads "minimize" and should read -- minimizes --
Line 49, reads "about 15 by" and should read -- about 15% by --

Column 6,
Line 51, reads "esters useful in the present invention contains" and should read -- esters useful in the present invention contain --

Column 7,
Line 11, reads "acrylate-baged" and should read -- acrylate-based --

Column 8,
Line 50, reads "chlorde" and should read -- chloride --
Line 66, "derivative" and should read -- derivatives --

UNITED STATES PATENT AND TRADEMARK OFFICE
CERTIFICATE OF CORRECTION

PATENT NO. : 6,300,390 B1
DATED : October 9, 2001
INVENTOR(S) : Christos Angeletakis It is certified that error appears in the above-identified patent and that said Letters Patent is hereby corrected as shown below:

Column 9,
Line 20, reads "DPEPA)" and should read -- (DPEPA) --
Line 36, reads "odecanediol" and should read -- dodecanediol --

Column 10,
Line 1, reads "eopentylgycol" and should read -- neopentylglycol --

Signed and Sealed this

Fourth Day of June, 2002

Attest:

JAMES E. ROGAN
Attesting Officer  Director of the United States Patent and Trademark Office